(12) United States Patent
Lorkowski

(10) Patent No.: US 6,312,297 B1
(45) Date of Patent: Nov. 6, 2001

(54) IMPLANTABLE ELECTRONIC UNIT

(75) Inventor: Lars Lorkowski, Berlin (DE)

(73) Assignee: BIOTRONIK MESS-und Therapiegeraete GmbH & Co. Ingenieurburo Berlin, Berlin (DE)

( * ) Notice: Subject to any disclaimer, the term of this patent is extended or adjusted under 35 U.S.C. 154(b) by 0 days.

(21) Appl. No.: 09/603,414

(22) Filed: Jun. 26, 2000

(30) Foreign Application Priority Data

Jun. 25, 1999 (DE) .............................................. 199 30 238

(51) Int. Cl.[7] .............................. H01R 4/48; H01R 4/28; H01R 9/22; H01R 13/73
(52) U.S. Cl. ........................... 439/838; 439/725; 439/907
(58) Field of Search .................................... 439/346, 372, 439/907, 359, 368, 370, 376, 725, 729, 838, 759, 263

(56) References Cited

U.S. PATENT DOCUMENTS

| 4,540,236 | 9/1985 | Peers-Trevarton . | |
|---|---|---|---|
| 4,898,173 | 2/1990 | Daglow et al. | 128/419 |
| 5,195,907 | * 3/1993 | Urban | 439/410 |
| 5,252,090 | 10/1993 | Giurtino | 439/441 |
| 5,261,395 | 11/1993 | Oleen et al. | 607/15 |
| 5,697,804 | 12/1997 | Froberg et al. | 439/346 |
| 6,019,647 | * 2/2000 | Trudel et al. | 439/864 |
| 6,132,390 | * 10/2000 | Cookston et al. | 600/585 |

FOREIGN PATENT DOCUMENTS 196 12 756   9/1997 (DE) .
WO 98/57702   12/1998 (WO) .

\* cited by examiner

Primary Examiner—Tulsidas Patel
Assistant Examiner—Chandrika Prasad
(74) Attorney, Agent, or Firm—Christie, Parker & Hale, LLP

(57) ABSTRACT

An implantable electronic unit (1, 30, 50), in particular a cardiac pacemaker, having at least one substantially socket-shaped connecting arrangement (3, 32, 33, 52, 53) arranged in the header (2, 31, 51) for a plug disposed at the proximal end of an electrode line (4, 34, 35, 54, 55), a plug receiving means (7, 60, 61) having a contact element (8, 20, 37, 38, 58, 59) for the deferent pole (6, 39, 40, 56, 57) of the plug, wherein the connecting arrangement includes a locking device (15) which secures the fit of the plug in relation to a tensile force acting in the axial direction and which can be operated by a hand lever (11) on the outside of the header. The locking device (15) includes the contact element (8, 20, 37, 38, 58, 59) and a locking cam (9, 36, 62, 63) mounted eccentrically in the connecting arrangement (3, 32, 33, 52, 53), wherein the resiliently arranged contact element embraces the deferent pole (6, 39, 40, 56, 57) of the plug in positively locking relationship and is in operative engagement with the locking cam (9, 36, 62, 63) in such a way that upon a rotary movement of the locking cam (9, 36, 62, 63) a variation in the position and/or the form of the contact element relative to the deferent pole (6, 39, 40, 56, 57) of the plug is forced for the purposes of making a force-locking connection between the deferent pole and the contact element.

18 Claims, 9 Drawing Sheets

IMPLANTABLE ELECTRONIC UNIT

FIELD OF THE INVENTION

An implantable electronic unit.

BACKGROUND OF THE INVENTION

U.S. Pat. No. 4,540,236 discloses an automatic locking device for a plug of a coaxial electrode line which is to be connected to a cardiac pacemaker. The device has hooked holding claws which engage into an annular groove at the tip of the plug and thereby provide that the plug connection is safeguarded in relation to axial tensile loadings. In order to be able to remove the plug from the connecting arrangement, pressure has to be applied manually from the end of the header in order to cause the holding claws to spread apart, by way of a linkage.

In addition, U.S. Pat. No. 5,252,090 discloses a self-locking plug connection for the plug of an implantable coaxial electrode line which has a connecting arrangement with an electrical contact element that has a plurality of resilient, substantially radially inwardly facing tongues which are urged radially outwardly by the tip of the plug against the spring force and produce a clamping force when the plug is pushed into the connecting arrangement. The electrical contact element has additional, inclinedly outwardly directed spring arms by which the clamping contact of the inwardly facing tongues at the tip of the plug can be disengaged when those spring arms are loaded from the exterior by a pressure force.

Furthermore, U.S. Pat. No. 5,697,804 discloses a cardiac pacemaker having a locking device in which the electrical contact element is in the form of a coil spring. By virtue of a rotary movement of the plug of the electrode line which is to be connected to the cardiac pacemaker, within the connecting arrangement, the diameter of the coil spring can be reduced to such an extent that a clamping action is produced between the individual turns of the coil spring and the peripheral surface of the deferent pole of the plug.

The known locking devices which are of a relatively complicated structure suffer from the disadvantage that they are very difficult to handle in service thereof, in particular when releasing the locking action, as the locking devices can only be released by a pressure force which is to be applied manually frontally or laterally from the header wall. In addition there is the disadvantage that it is not possible to see whether the plug disposed in the connecting arrangement has also actually been locked.

Finally, international patent application WO 98/57702 discloses a screw-free connecting system for connecting at least one electrode line to a cardiac pacemaker. The header of the cardiac pacemaker has a locking device with a hand lever connected to a stepped shaft, for locking a connected electrode line. The shaft which is rotatable by the hand lever extends transversely with respect to the axis of the bore or bores provided for insertion of the electrode line, and has, distributed at its periphery, saddle-shaped recesses of different depths which are disposed in pairs in mutually orthogonally opposite relationship. In the open position of the locking device the large recesses in the rotatable shaft form a part of the bore wall and bear against the sheathing of the electrode line or lines. By virtue of pivotal movement of the hand lever the smaller recesses in the shaft come into operative contact with the sheathing of the electrode line or lines, with a reduction in the free cross-section of the bore, and block the electrode line or lines to prevent axial movement, by virtue of a clamping action.

That locking device is in the form of a complicated shaped component and suffers from the further disadvantage that the clamping action of the shaft for holding the plug or plugs is limited to the region of the insulation of the electrode line. As a result, the arrangement essentially only affords a mechanical safeguard in relation to tensile forces acting on the electrode line, without the actual contact locations having to be inevitably secured. It is therefore not possible to have any information about the quality of the contacting action if the plug of the electrode line for example does not reach or only partially reaches the contact region which is provided for same, after insertion of the line. In addition, there is the disadvantage that damage to the wire strands in the line or a short-circuit between individual strands cannot be reliably excluded.

SUMMARY OF THE INVENTION

The present invention is an implantable electronic unit having a locking device for the plug of a coaxial electrode line which can be connected to the unit, by which, with simple means, the inserted plug can be fixed with a substantially axially directed tensile loading acting on the electrode line, and at the same time good contact is reliably achieved.

When using an eccentric crank arrangement which can be activated manually by a lever, a large force can be caused to act by virtue of the lever action upon just a relatively slight pivotal movement, by the eccentric, and that force can preferably be used to produce clamping forces between two bodies. By suitable selection of the degree of eccentricity and the shape of the eccentric, it is possible to conveniently control the clamping force produced, in dependence on the magnitude of the pivotal angle.

In accordance with the invention the substantially socket-shaped connecting arrangement which is disposed in the header of an implantable electronic unit, preferably a cardiac pacemaker, for the plug of a coaxial electrode line, has a locking device which is formed from a manually actuable, eccentrically mounted locking cam and a contact element provided in the connecting arrangement for the deferent pole of the plug of a coaxial electrode line to be connected to the cardiac pacemaker.

The eccentrically mounted locking cam is in operative engagement at its edge with the contact element so that a rotary movement of the locking cam is transmitted to the contact element. In that way the contact element which embraces the deferent pole of the plug in positively locking relationship is reversibly deformed in such a way that a force-locking connection is produced between that pole and the contact element, the connection fixing the plug within the connecting arrangement and at the same time ensuring an improved galvanic contact between the contact element and the deferent pole of the plug.

In accordance with the preferred embodiment of the invention the contact element is secured to the plug receiving means of the connecting arrangement by welding. The contact element which comprises a spring material is of a tongue-shaped configuration and extends substantially transversely with respect to the longitudinal axis of the connecting arrangement. It has a bore through which the deferent pole of the plug disposed in the connecting arrangement is passed.

In accordance with the preferred embodiment of the invention the eccentrically mounted locking cam is of a substantially disk-shaped configuration, it is mounted using a mounting journal or trunnion in the header and it is connected to the hand lever arranged at the side wall of the header, for producing a rotary movement.

The axis of rotation of the eccentrically mounted locking cam extends substantially perpendicularly to the axis of the plug of the electrode line so that the free end of the contact element is supported on the edge of the eccentrically mounted locking cam. As the spacing of the edge changes in relation to the axis of rotation of the locking cam in the rotary movement, the contact element which is of a resilient nature is reversibly deformable by a rotary movement of the locking cam, which is produced by pivotal movement of the hand lever, and in that case is moved relative to the deferent pole of the plug, producing a force-locking connection, in particular a clamping connection, thereto.

The force-locking connection is produced in a simple manner in that the free diameter of the bore in the contact element, said diameter being determined by projection on to the cross-sectional area of the deferent pole, is reduced. By virtue of a clamping action, at just a relatively slight deflection of the contact element, that produces a sufficiently great holding force between the deferent pole and the contact element, for fixing the plug in relation to an axial tensile loading on the coaxial electrode line.

In accordance with the preferred embodiment of the invention the eccentrically mounted locking cam is substantially in the form of a circular disk, whereby it is possible to produce a particularly uniform clamping force. At the same time, the use of the hand lever provides that the amount of force applied for producing the clamping force required for fixing the plug is relatively slight.

This means that the action of locking the plug of a coaxial electrode line in a cardiac pacemaker to be implanted can be very conveniently implemented, which is an aspect of particular advantage for example under the conditions of an operation.

An advantageous development of the invention provides that the contact element for producing the clamping action by reversible deformation is transferred by means of the eccentrically mounted locking cam from a released condition into a locked condition.

As in accordance with a variant of the invention a range of rotary movement of preferably 90° is provided for the locking cam, the hand lever which for operation of the locking device is arranged at the outside of the header and which is connected to the locking cam is in a position of being substantially perpendicular to the axis of the connecting arrangement when the locking device is opened. When the locking arrangement is closed the hand lever extends substantially parallel to the axis of the connecting arrangement and is therefore adapted to the shape of the header in a manner which is advantageous in particular in terms of implantation of the cardiac pacemaker.

It is thus possible easily to ascertain the respective locking condition from the position of the hand lever, which is of additional advantage for practical use of the locking device according to the invention.

In accordance with another advantageous development of the invention, provided on the outside of the header and the side of the free end of the hand lever, which is towards the header, are respective retaining or detent means which, when the locking device is closed, are in force-locking and/or positively locking engagement and fix the hand lever to prevent an unwanted return movement which results in opening of the locking device. The retaining means are in the form of a projection and a recess of corresponding size for receiving the projection.

In accordance with an additional variant of the invention the contact element is of a two-part nature, wherein provided in each of the portions is a bore for receiving the deferent pole of a respective plug disposed in a connecting arrangement. That makes it easily possible, with an eccentrically mounted locking cam, to simultaneously form a respective locking device for each of the plugs of two electrode lines.

The two portions of the contact element are coupled together by a connector of plastic material as the plugs of the individual coaxial electrode lines carry different potentials and potential equalization must be avoided.

In accordance with another advantageous embodiment of the invention the eccentrically mounted locking cam is arranged between two connecting arrangements which are of substantially similar configuration and which are positioned in vertically superposed relationship. The contact elements provided on the connecting arrangements are of a similar configuration and, with a substantially mirror-image symmetrical arrangement, for the purposes of forming a locking device, respectively bear against the locking cam. Upon a rotary movement of the eccentrically mounted locking cam, which is afforded by way of the hand lever, the contact elements simultaneously effect a pivotal movement in opposite directions so that it is possible to produce the clamping force required for fixing the corresponding plug, at both different poles, by virtue of a movement of the hand lever.

In accordance with an additional embodiment of the invention, equally advantageous actuation of two locking arrangements can be achieved if a separate, respectively eccentrically mounted locking cam is provided for each connecting arrangement, wherein the first locking cam has a connection to a hand lever and the rotary movement of the first locking cam is transmitted from same in force-locking and positively locking relationship to the second locking cam. For the purposes of convenient transmission of the rotary movement the two eccentrically mounted locking cams each have a mounting journal or trunnion which carries an external tooth arrangement, at least at a portion of the periphery thereof.

In accordance with a variant of the invention, for the purposes of transmitting the rotary movement, there is provided an indirect connection between the locking cams, which indirect connection can preferably be implemented by means of a pinion which connects together the mounting journals or trunnions of the locking cams, forming a transmission assembly.

Other advantageous developments of the invention are characterized in the appendant claims and are illustrated in greater detail hereinafter together with the description of the preferred embodiment of the invention with reference to the drawings in which:

DETAILED DESCRIPTION OF THE INVENTION

Figure 1A:
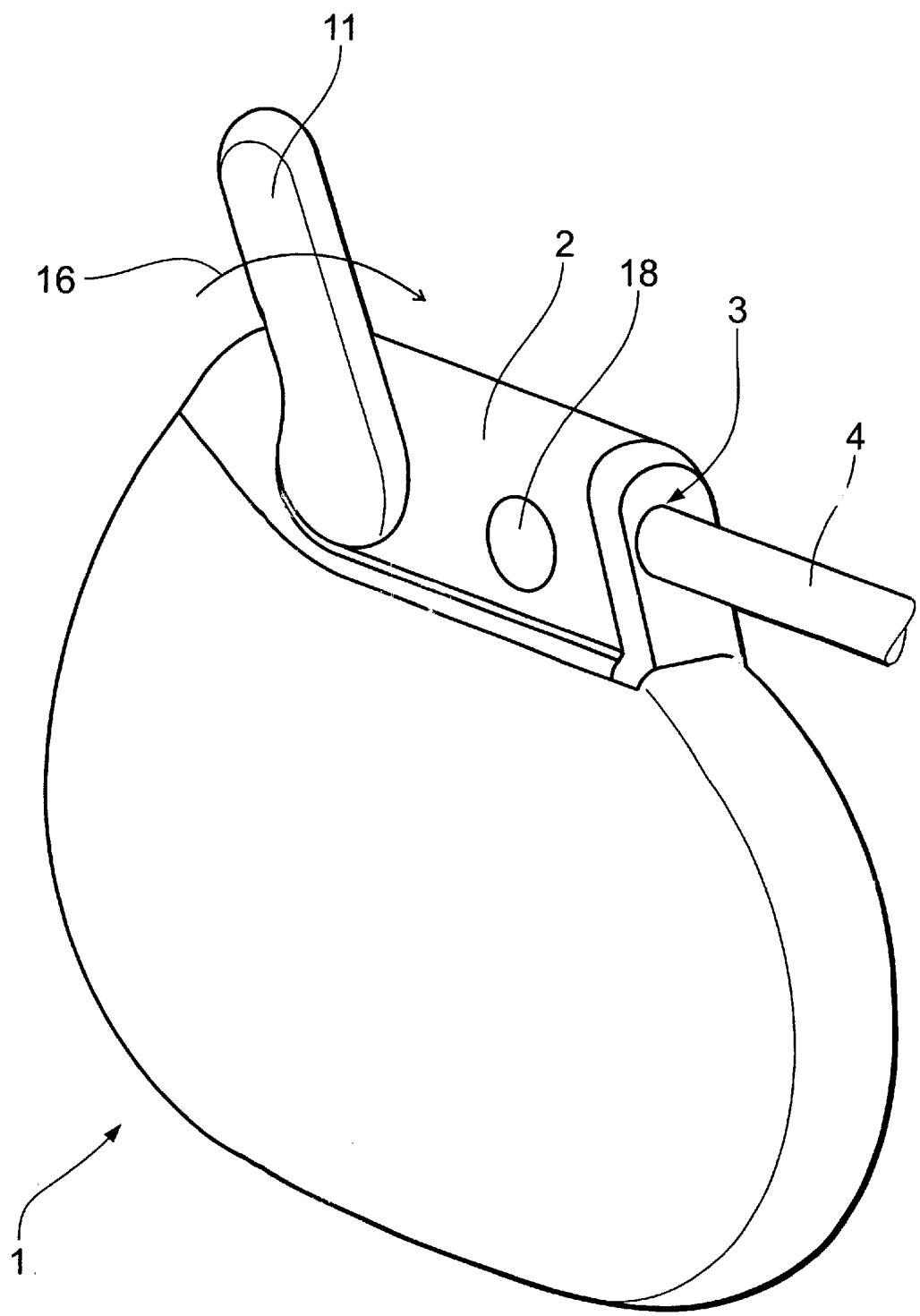
FIG. 1a is a perspective side view of a preferred embodiment of the invention with the locking device in the opened condition.
Figure 1B:
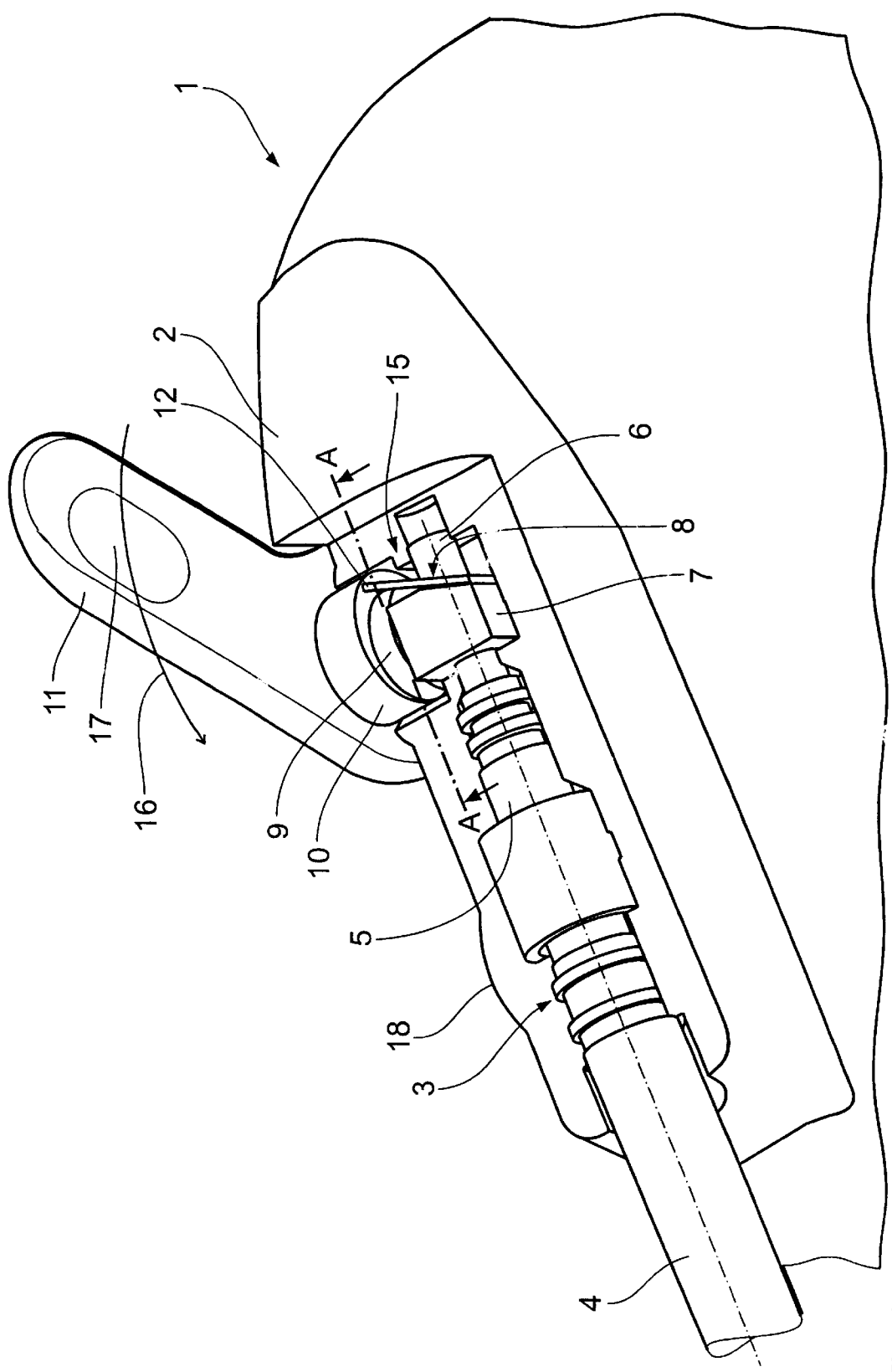
FIG. 1b is a perspective view of part of the embodiment of the invention as shown in FIG. 1a, with the header in the opened condition.

The implantable electronic unit 1 shown in FIGS. 1a and 1b; e.g., a cardiac pacemaker, has a header 2 in which is arranged a connecting socket 3, by way of which a coaxial electrode line 4 is electrically connected to the implantable electronic unit 1 by means of a standardized IS-1 plug 5.

The deferent pole 6 of the plug 5 which is inserted into the connecting socket 3, at the proximal end of the coaxial electrode line 4, is disposed in a plug receiving means 7 which is provided within the connecting socket 3. At its side opposite to the insertion opening for the plug 5, the plug receiving means 7 has a contact element 8. The contact element 8 is of a tongue-shaped configuration and comprises a spring plate. The contact element 8 is secured at one side to the wall of the plug receiving means 7, preferably by welding, in such a way that the axis of the contact element extends substantially transversely with respect to the longitudinal axis of the plug receiving means 7 or the plug 5.

Arranged at the wall of the plug receiving means, which is disposed in the direction in which the contact element 8 extends, is a locking cam 9 which is in the form of an eccentric and which is connected to a hand lever 11 by way of a mounting journal or trunnion 10 mounted in the wall of the header 2. The diameter of the locking cam 9 is so selected that the free end 12 of the contact element 8 bears against the flank thereof (see reference 13 in FIG. 1d).

Provided in the contact element 8 which is resiliently secured to the plug receiving means 7 is a bore (see reference 14 in FIG. 1c), through which the deferent pole 6 moves when the plug 5 is inserted into the connecting socket 3 for connecting the coaxial electrode line 4 to the implantable electronic unit 1.

The contact element 8 and the locking cam 9 form the elements of a locking device 15 which can be activated by pivotal movement of the hand lever 11 in the direction of the arrow 16, and which can be moved from an opened condition in which the plug 5 can be pushed into or withdrawn from the connecting socket 3, into the closed condition in which a plug 5 in the connecting socket 3 is secured against unwanted sliding movement out of the connecting socket 3, which movement could be caused by a tensile force component acting in the axial direction.

When the locking device 15 is in the closed condition, the co-operation of the eccentric cam with the contact element 8 produces between the deferent pole 6 and the contact element 8 a clamping force which fixes the pole 6 of the plug 5 in the plug receiving means 7.

References 17 and 18 denote retaining or detent means, in the form of a recess and a projection respectively, on the outside of the header 2 and at the inside of the hand lever 11. The retaining means come into operative engagement when the hand lever is pivoted in the direction of the arrow 16 to close the locking device 15. That ensures in a simple fashion that the hand lever is fixed in that position, to resist unwanted return movement.

Figure 1C:
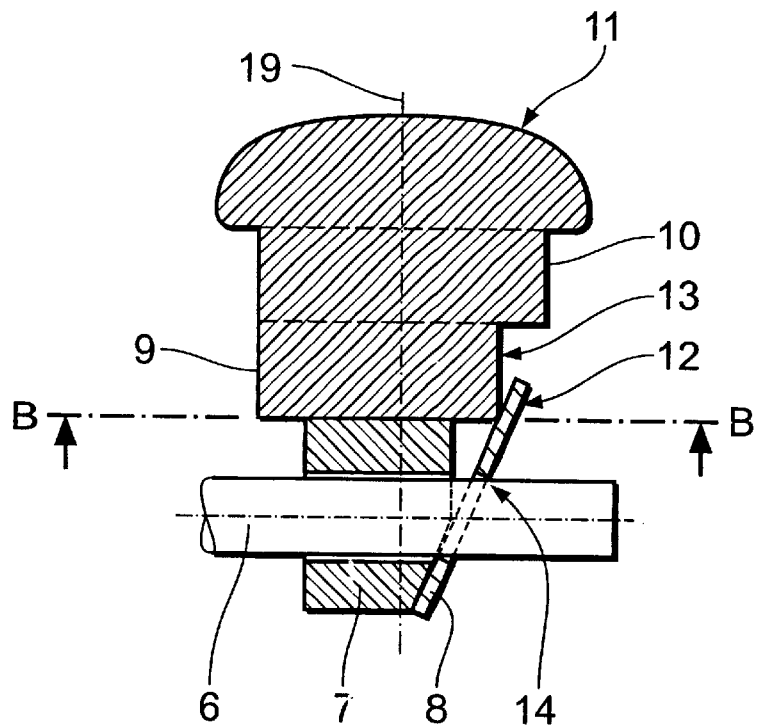
FIG. 1c shows the view of a section taken along line A—A in FIG. 1b.
Figure 1D:
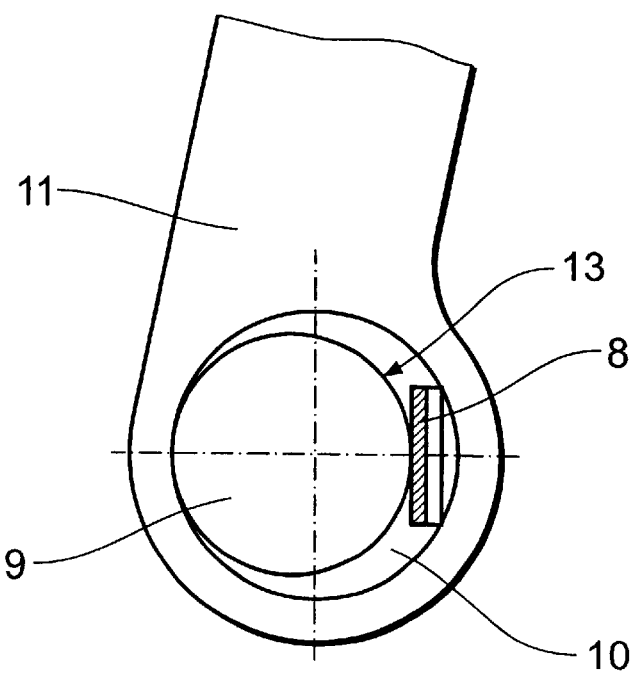
FIG. 1d shows the view of a section taken along line B—B in FIG. 1c.

FIGS. 1c and 1d show the structure and the mode of operation of the locking device which is formed from the contact element 8 and the eccentric cam 9.

Figure 2A:
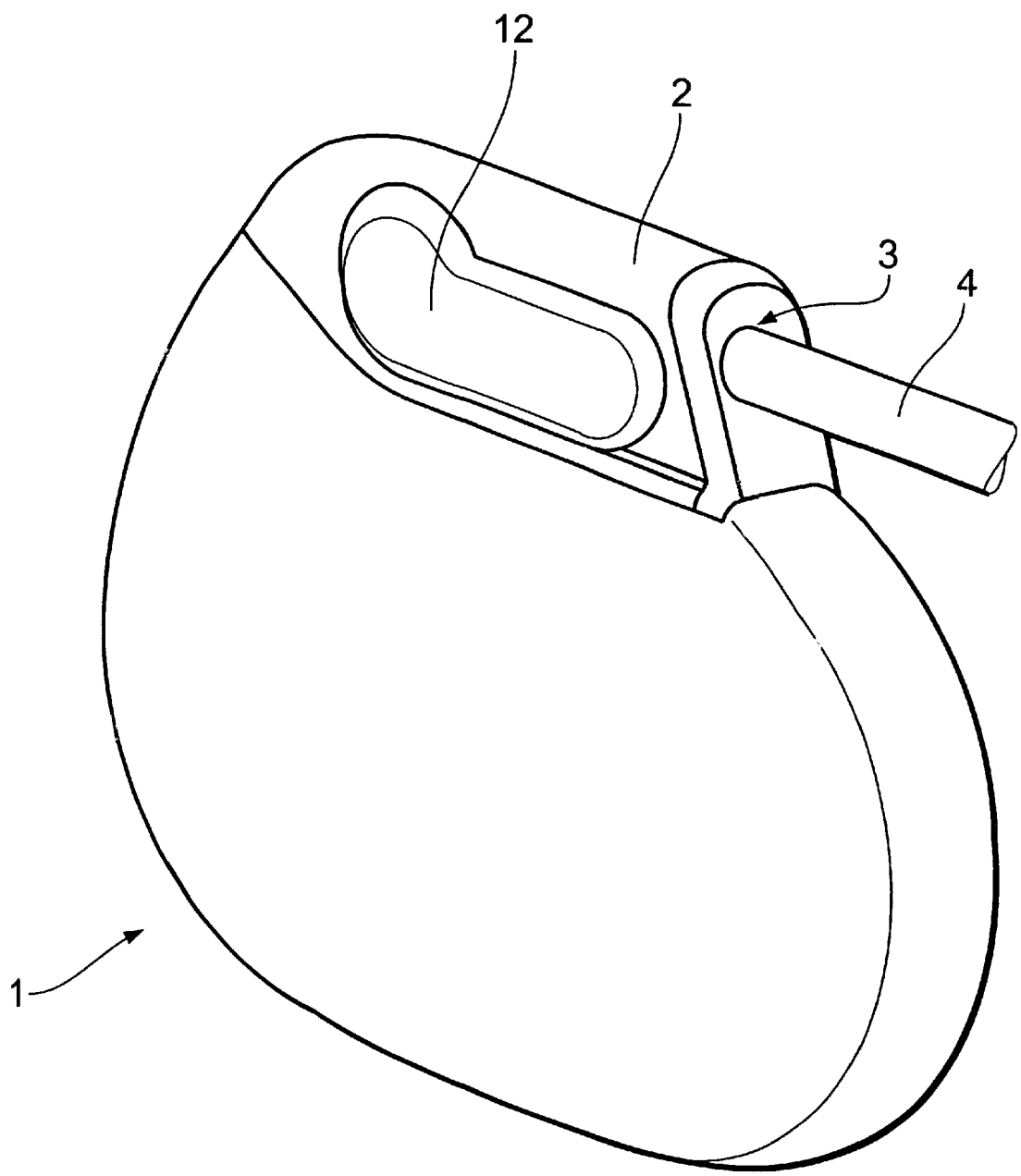
FIG. 2a is a perspective side view of the embodiment of the invention as shown in FIG. 1a with the locking device in the closed condition.
Figure 2B:
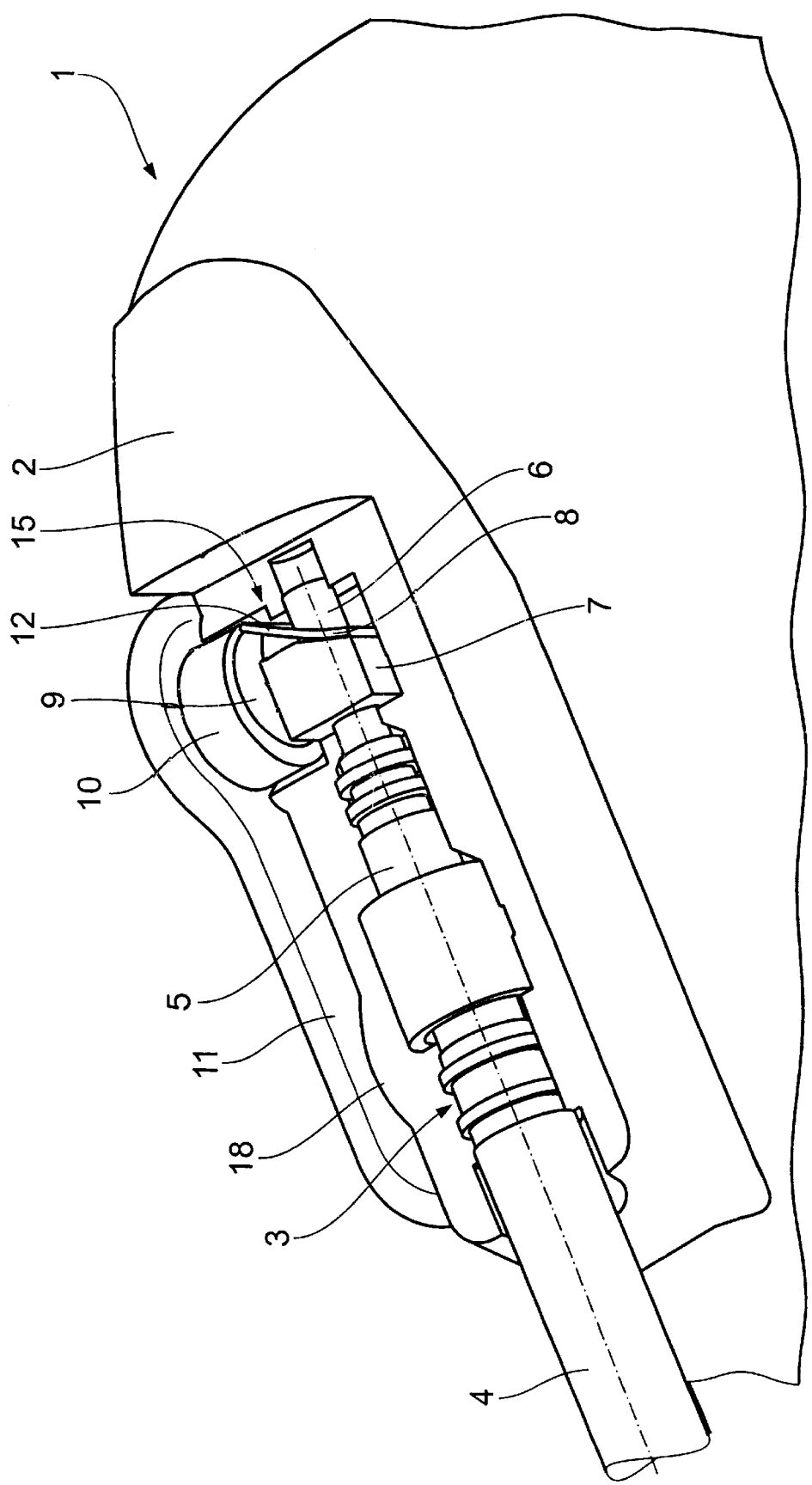
FIG. 2b is a perspective view of part of the embodiment of the invention as shown in FIG. 2a, with the header in the opened condition.
Figure 2C:
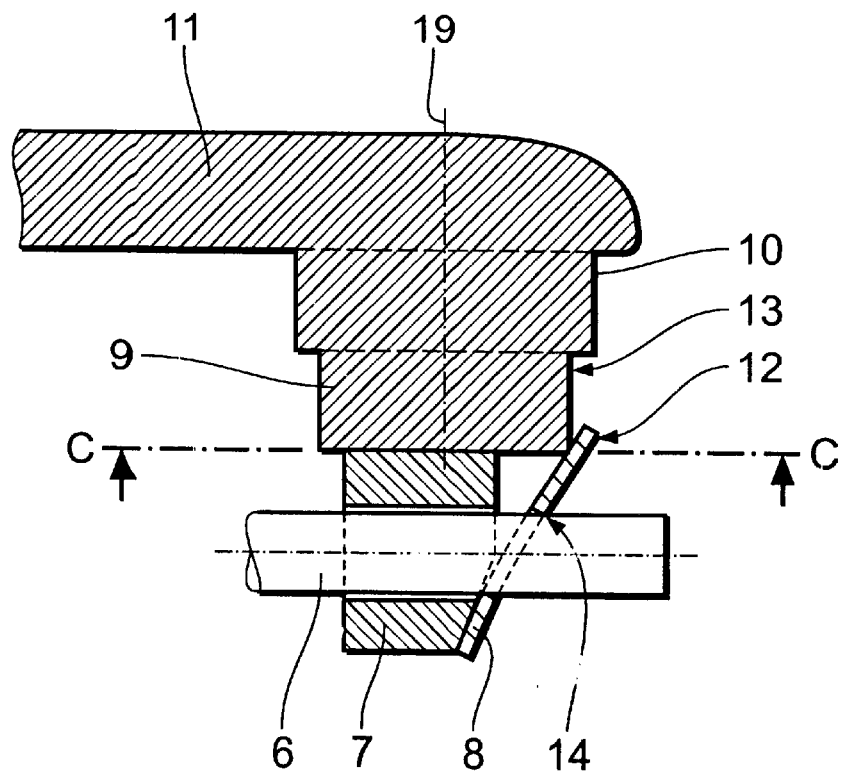
FIG. 2c shows the view of a section taken along line C—C in FIG. 2b.
Figure 2D:
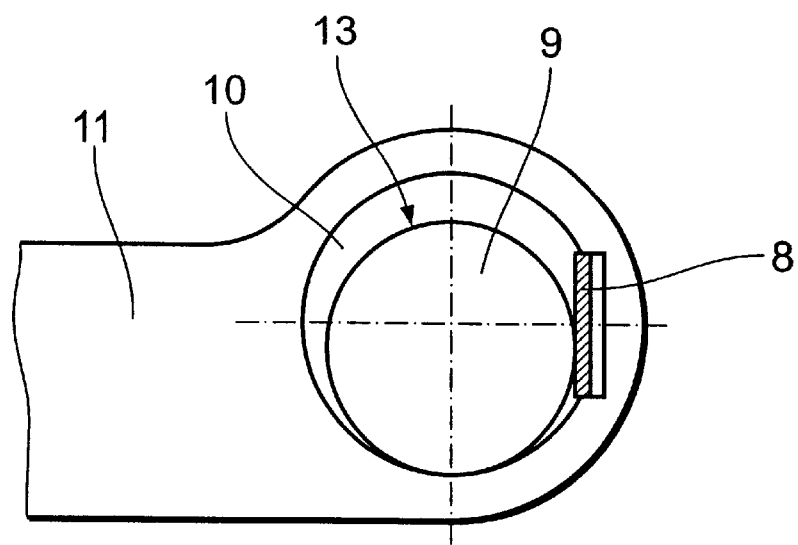
FIG. 2d shows the view of a section taken along line D—D in FIG. 2c.

The contact element 8 which is secured to the plug receiving means 7 has a bore 14 which, when the locking device is opened, is of a free cross-section of adequate size, through which the pole 6 of the plug can move when the latter is pushed into the connecting socket. After pivotal movement of the hand lever 11 which is supported in the header by the mounting trunnion 10, about the axis 19 which extends transversely with respect to the longitudinal axis of the connecting socket, the contact element 8 which bears against the flank 13 of the eccentric cam is reversibly deformed. That deformation (see the views in FIGS. 2c and 2d) causes a force-locking connection to be made between the contact element 8 and the deferent pole 6 of the plug, which is in the plug receiving means 7.

The respectively prevailing locking condition of the locking device 15 can be easily ascertained by considering the position of the hand lever 11. When the hand lever is disposed substantially transversely with respect to the longitudinal axis of the connecting socket 3, the locking device is opened. A hand lever which extends parallel to the longitudinal axis of the connecting socket indicates that the locking device is closed.

Due to the length of the hand lever 11, the amount of force required to produce the clamping force for fixing the plug in the connecting socket 3, between the contact element 8 and the deferent pole 6 is relatively slight, which is an aspect of advantage in terms of the practical situation of use, for example under the conditions of operation in a medical establishment.

FIGS. 2a, 2b, 2c and 2d show the positions of the elements 8 and 9 of the locking device 15 when the latter is in the closed condition.

The hand lever 11 is folded in the direction of the coaxial electrode line 4 (see reference 16 in FIG. 1) so that the end 12 of the resilient contact element 8, which bears against the flank 13 of the eccentric cam 9, moves towards the right in the plane of the drawing in the respective Figure, whereby the free diameter of the bore 14, being determined by projection on to the cross-sectional area of the pole 6, is reduced. By virtue of a clamping action, that produces a sufficiently high holding force between the deferent pole 6 and the contact element 8 upon an axial tensile loading on the electrode line 4. The appropriate tensile force is applied to the wall of the header 2 by way of the contact element 8, by way of the plug receiving means 7 or the eccentric cam 9.

Figure 3:
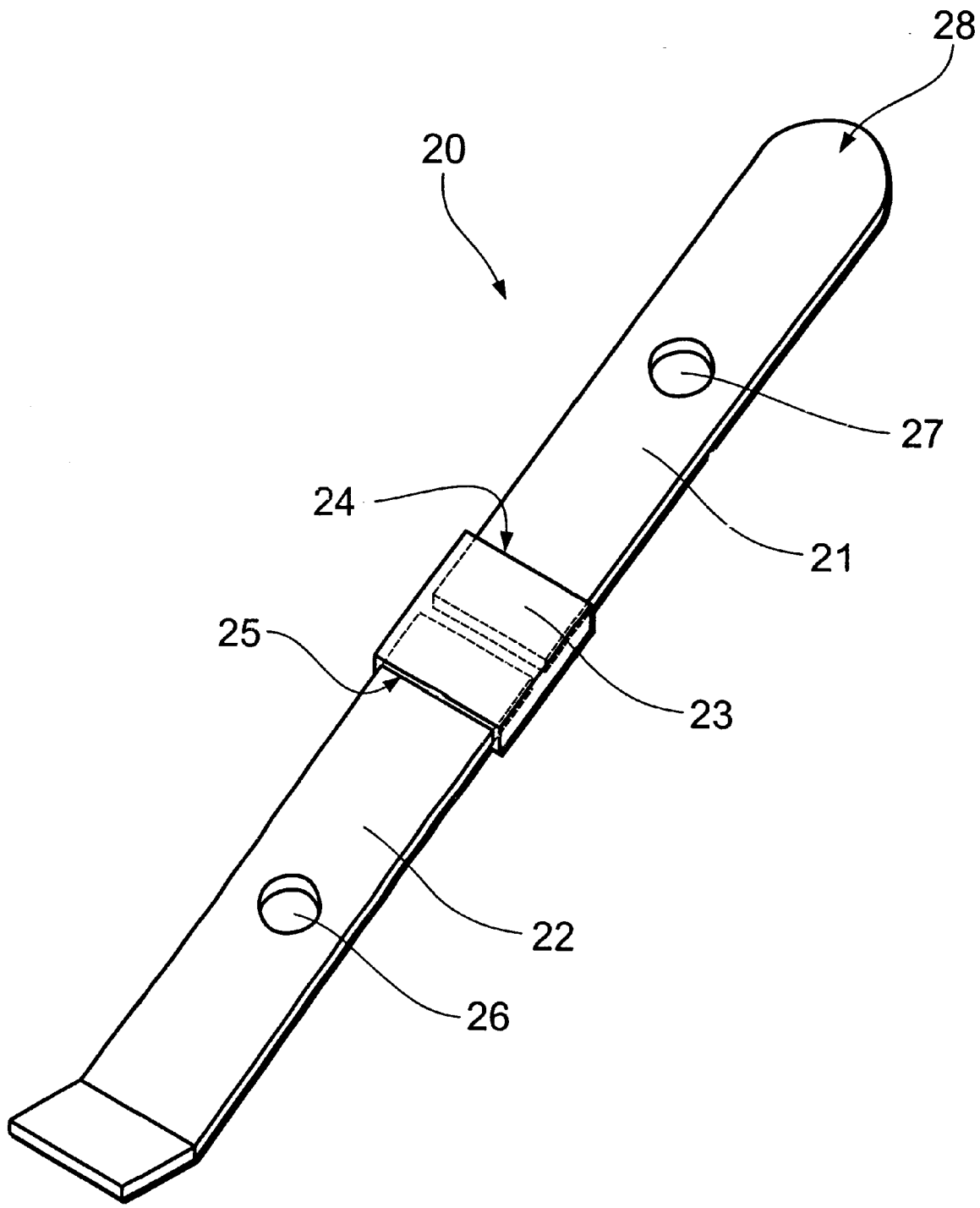
FIG. 3 shows an advantageous development of the invention.

FIG. 3 shows a contact element 20 which is made from a metal spring material and which comprises two portions 21 and 22 which are connected together in mutually electrically insulated relationship. Provided for connecting the two portions is a coupling portion 23 with two insertion pockets 24 and 25, into which an end of each of the portions 21 and 22 are respectively pressed and/or glued in such a way that the spring and flexural properties of the entire contact element 20 do not substantially differ from a contact element which is formed in one piece. The bores 26 and 27 can each receive a respective deferent pole of the plug of a coaxial electrode line so that, by virtue of a rotary movement of a locking cam engaging the free end 28 of the contact element 20 (see reference 9 in FIGS. 1c and 2c), both plugs can be simultaneously secured in the corresponding connecting arrangement, to prevent them from sliding out in an unwanted fashion.

Figure 4:
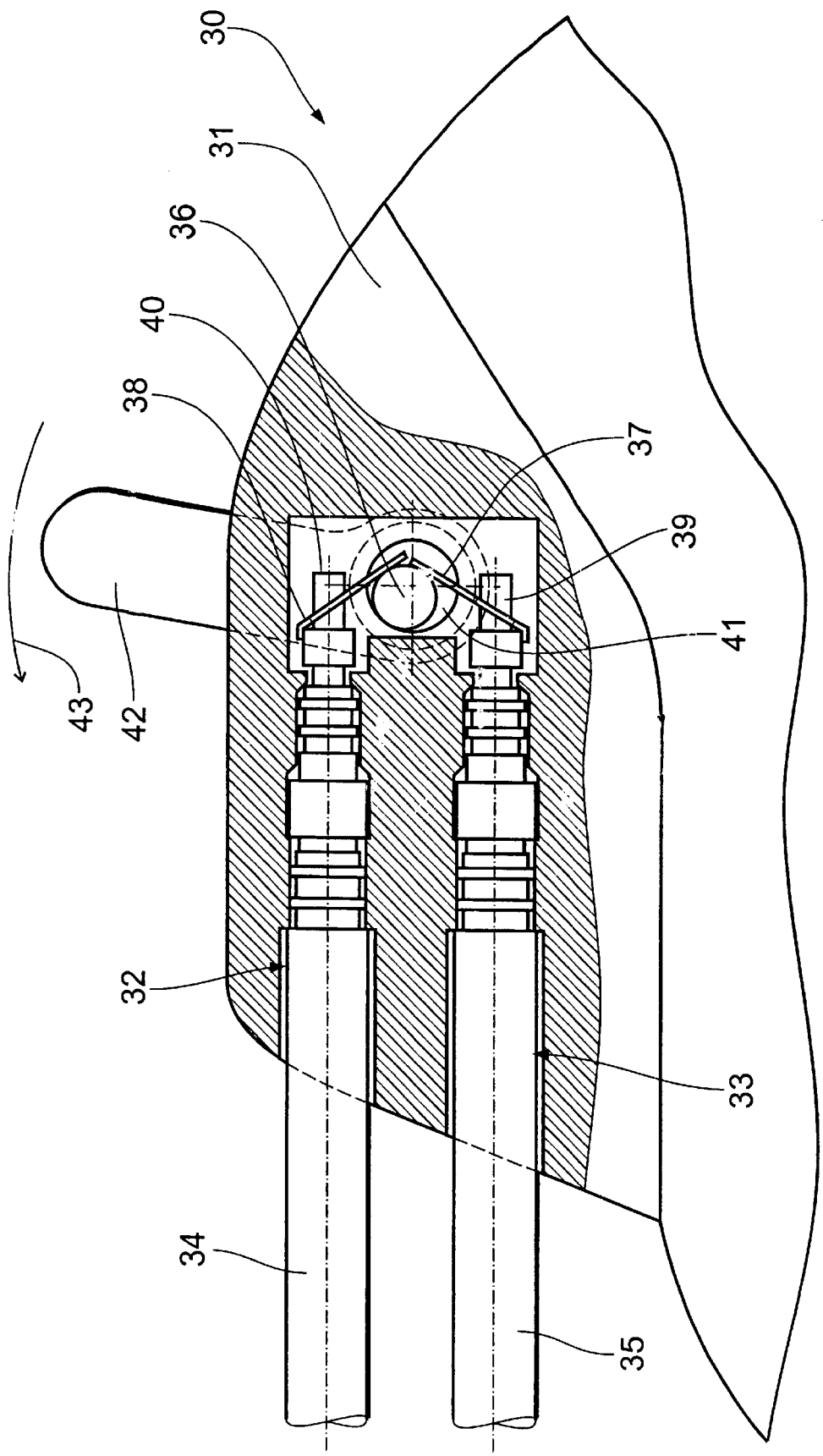
FIG. 4 shows another advantageous embodiment of the invention illustrating a partial view in longitudinal section through a connecting arrangement.

The implantable electronic unit 30 shown in FIG. 4 has a header 31 with two connecting sockets 32 and 33 for a respective plug of a coaxial electrode line 34, 35.

The locking cam 36 which is in the form of an eccentric cam is disposed in operative contact with two contact elements 37 and 38 which are arranged substantially in mirror-image symmetrical relationship with each other. The deferent poles 39, 40 of the plugs are passed through a bore (not referenced) in the respective contact element and are held within that bore by a clamping action when the hand lever 42 which is connected to the eccentric cam 36 by way of the mounting trunnion 41 is pivoted in the direction of the arrow 43.

The structure which is shown in FIG. 4 in the unlocked condition provides that two plugs can be simultaneously secured to prevent unintentional release thereof from the connecting sockets 32, 33, with a pivotal movement of the hand lever 42.

Figure 5:
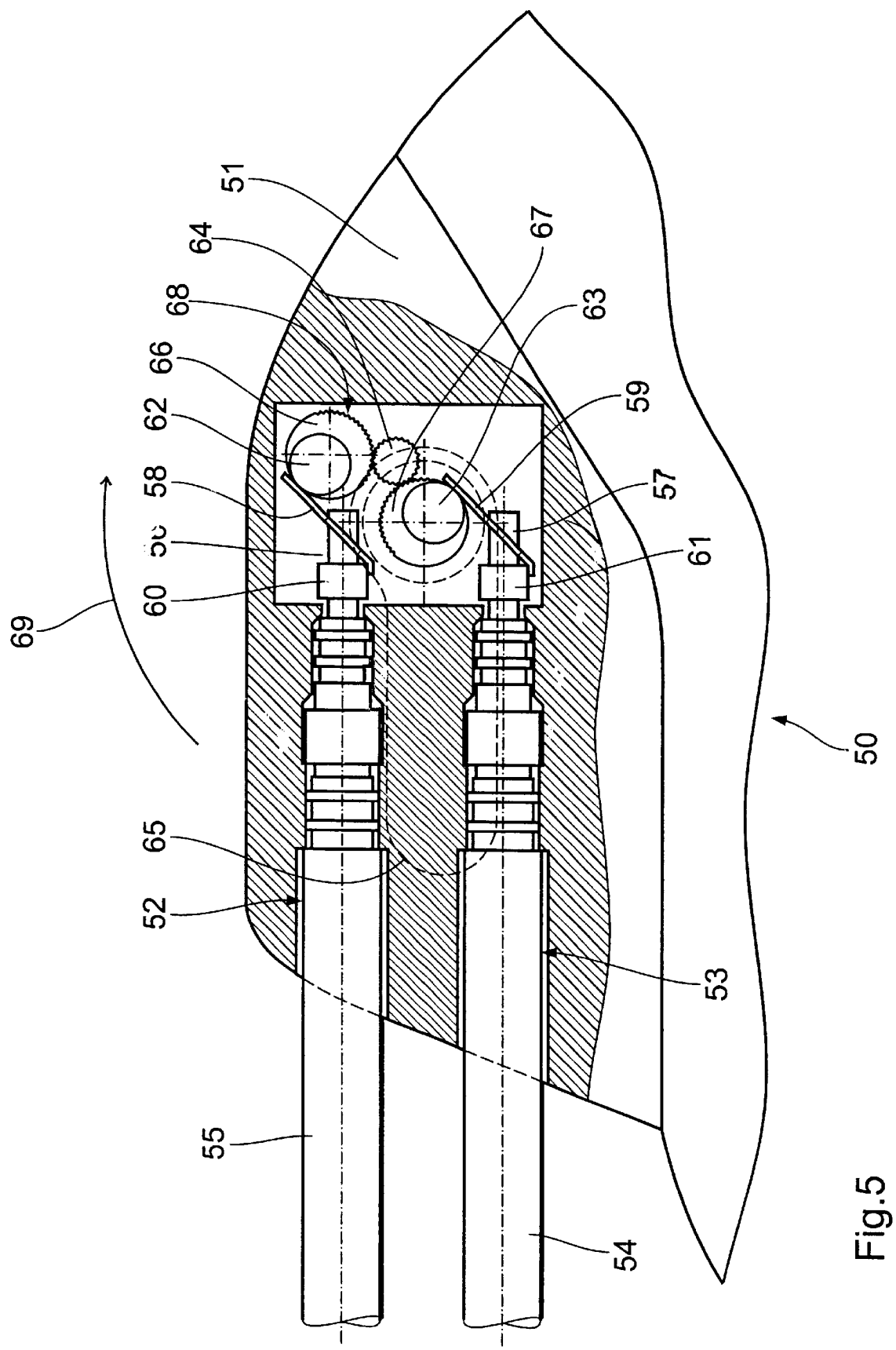
FIG. 5 is a partial view in longitudinal section of an advantageous variant of the embodiment of the invention as shown in FIG. 4.

Provided for the implantable electronic unit 50 shown in FIG. 5 is a header 51 having two connecting sockets 52 and 53, in each of which is disposed the plug of a respective coaxial electrode line 54, 55. The deferent poles 56, 57 of the plugs are shown in their position of being fixed by the respective locking device.

A weld join is provided for connecting the electrical contact elements 58 and 59 to the respective plug receiving means 60 and 61. The contact elements extend parallel to each other. To form the locking devices for fixing the deferent poles 56, 57, associated with each of the contact elements 58, 59 is an eccentric cam 62, 63, against which the free ends of the contact elements 58, 59 bear.

The eccentric cam 62 is driven indirectly by way of a pinion 64 when the eccentric cam 63 turns upon pivotal movement of the hand lever 65. To form the appropriate transmission arrangement, the mounting trunnions 66, 67 of the eccentric cams 62, 63 carry an external tooth arrangement 68. To ensure the transmission function for the transmission of force by way of the movement of the hand lever 65, it is sufficient if the external tooth arrangement extends over half the periphery of the mounting trunnions 66, 67.

When the hand lever 65 is moved in the direction of the arrow 69, the contact elements 58, 59 are relieved of the pressure of the respective eccentric cam 62, 63. When that happens, the contact element 58 or 59 respectively pivots with its free end slightly downwardly and upwardly respectively in the plane of the drawing, whereby the force-locking connection between the contact elements 58, 59 and the deferent poles 56, 57 is disengaged and the respective plug of the electrode lines 54, 55 can be conveniently withdrawn from the connecting socket 52, 53. Release of the two locking devices is effected simultaneously by a single rotary movement of the lever through about 90°, in which respect the released condition of the locking device can be clearly seen by virtue of the substantially perpendicular position of the hand lever 65 on the outside wall of the header 51.

Fixing of the hand levers 42 and 65, which are shown in FIGS. 4 and 5, to prevent an unwanted reverse movement out of a position of locking the locking devices, is effected by retaining or detent means (not shown), in the manner already described in the description relating to FIG. 1b.

Fixing of both plugs in the connecting sockets 32, 33 and 52, 53 respectively by means of a pivotal movement of the hand lever 42 and 65 respectively, with the application of a relatively small amount of force, is of particular advantage in terms of practical use, for example under the conditions of an operation in a medical establishment.

For reasons of clarity, FIGS. 1b, 2b, 4 and 5 do not include an illustration of the electrical line connection from and to the electronic units 1, 30 and 50, respectively.

The invention is not limited in terms of the implementation thereof to the preferred embodiments set forth hereinbefore by way of example. On the contrary, it is possible to envisage a number of variants which make use of the illustrated structure even in configurations of a basically different kind.

What is claimed is:

1. An implantable electronic unit comprising;
   a header;
   at least one substantially socket-shaped connecting arrangement arranged in the header for receiving a plug with at least one deferent pole disposed at the proximal end of an electrode line;
   a plug receiving means having a resiliently arranged contact element for the at least one deferent pole of the plug;
   a locking device provided at the connecting arrangement to secure the fit of the plug, the locking device including the contact element and a locking cam mounted eccentrically in the connecting arrangement; and
   a hand lever on the outside of the header for operating the locking device;
   wherein the resiliently arranged contact element embraces the deferent pole of the plug, and is in operative engagement with the locking cam in such a way that upon a rotary movement of the locking cam a variation in one of the position and the form of the contact element relative to the deferent pole of the plug is forced, in order to make a force-locking connection between the deferent pole and the contact element for the purposes of fixing the plug and making a galvanic contact.

2. The electronic unit as set forth in claim 1 further comprising a locking cam in the form of a disk.

3. The electronic unit as set forth in claim 2 wherein the locking cam extends transversely with respect to the longitudinal axis of the plug.

4. The electronic unit as set forth in claim 2 or claim 3 wherein the axis of rotation of the locking cam extends transversely with respect to the longitudinal axis of the plug.

5. The electronic unit as set forth in claim 1 wherein the contact element is in the form of a tongue-shaped spring plate which is fixed at one side, preferably at the connecting arrangement, and extends substantially transversely with respect to the longitudinal axis of the plug.

6. The electronic unit as set forth in claim 5 wherein the contact element has a bore through which the deference pole of a plug disposed in the plug receiving means is passed.

7. The electronic unit as set forth in claim 1 wherein the contact element is supported with its free end on the cam path of the eccentrically mounted cam in such a way that upon rotation of the locking cam, by virtue of pivotal movement of the contact element, the free diameter of the bore which is required for the deferent pole upon insertion of the plug is reduced and the deferent pole is fixed by a clamping force to the contact element.

8. The electronic unit as set forth in claim 7 wherein the contact element is transferred from a released condition into a locked condition to produce the clamping action by reversible deformation by means of the locking cam.

9. The electronic unit as set forth in claim 6 wherein the locking cam has a range of rotary movement of preferably 120°.

10. The electronic unit as set forth in claim 1 further comprising retaining means on the outside of the header and the side of the hand lever towards the header, respectively, which, when the locking device is closed, are in engagement in force-locking and/or positively locking relationship and fix the hand lever against an unwanted reverse movement resulting in opening of the locking device.

11. The electronic unit as set forth in claim 10 wherein the retaining means are in the form of a projection and a recess of corresponding size for receiving the projection.

12. The electronic unit as set forth in claim 1 wherein the contact element includes two tongue-shaped spring plate portions coupled together by a connector of plastic material wherein each of the tongue-shaped spring plate portions have a bore for receiving the deferent pole of a respective plug disposed in a connecting arrangement.

13. The electronic unit as set forth in claim 1 wherein the locking cam is arranged between two connecting arrangements which are of substantially similar configuration and which are positioned in vertically mutually superposed relationship and whose contact elements respectively bear against the locking cam, in a substantially mirror-image symmetrical relationship, for the purposes of forming a respective locking device.

14. The electronic unit as set forth in claim 13 further comprising a separate locking cam for each connecting arrangement, wherein the first locking cam is connected to a hand lever and the rotary movement of the first locking cam is transmitted from the latter to the second locking cam in force-locking and positively locking relationship.

15. The electronic unit as set forth in claim 14 wherein the locking cams each have a respective mounting trunnion with an external tooth arrangement on at least a portion of the periphery thereof.

16. The electronic unit as set forth in claim 15 wherein the locking cams are connected indirectly for transmission of the rotary movement.

17. The electronic unit as set forth in claim 16 wherein the external tooth arrangement of the mounting trunnions of the locking cams is in engagement directly or by way of a pinion.

18. The electronic unit as set forth in claim 1, wherein the electronic unit is a cardiac pacemaker.

* * * * *